United States Patent [19]

Boden

[11] 4,384,007
[45] May 17, 1983

[54] USE IN FLAVORS OF PRINS REACTION PRODUCTS OF DIISOBUTYLENE

[75] Inventor: Richard M. Boden, Monmouth Beach, N.J.

[73] Assignee: International Flavors & Fragrances Inc., New York, N.Y.

[21] Appl. No.: 391,593

[22] Filed: Jun. 24, 1982

Related U.S. Application Data

[62] Division of Ser. No. 280,683, Jul. 6, 1981.

[51] Int. Cl.³ .............................................. A23L 1/226
[52] U.S. Cl. ................................. 426/534; 252/522 R; 131/276
[58] Field of Search ........................................ 426/534

[56] References Cited

FOREIGN PATENT DOCUMENTS 2108805  8/1971  Fed. Rep. of Germany .

OTHER PUBLICATIONS

Hirai et al., Chemical Abstracts, 65:2114f, 1966.

Primary Examiner—Joseph M. Golian
Attorney, Agent, or Firm—Arthur L. Liberman

[57] ABSTRACT

Described for augmenting or enhancing the aroma or taste of foodstuffs, chewing gums, toothpastes, chewing tobaccos and medicinal products are certain prins reaction products and derivatives thereof of diisobutylene defined according to the generic structure:

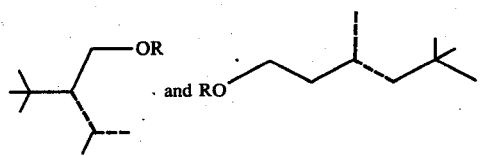

wherein one of the dashed lines represents a carbon-carbon double bond and the other of the dashed lines represents a carbon-carbon single bond and wherein R represents hydrogen or acetyl.

3 Claims, No Drawings

4,384,007

USE IN FLAVORS OF PRINS REACTION PRODUCTS OF DIISOBUTYLENE

This application is a divisional of application for United States letters Pat. Ser. No. 280,683 filed on July 6, 1981.

BACKGROUND OF THE INVENTION

The present invention relates to Prins reaction products of diisobutylene and derivatives thereof defined according to the genera:

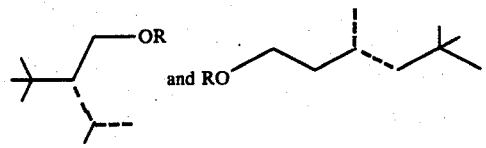

wherein one of the dashed lines represents a carbon-carbon double bond and the other of the dashed lines represent a carbon-carbon single bond, and wherein "R" represents hydrogen or acetyl and to novel compositions using such Prins reaction products or derivatives thereof to augment or enhance the flavor and/or aroma of consumable materials or to impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply, and to provide more uniform properties in the finished product.

Spicy, cumin oil-like, green and herbaceous aroma and taste nuances are particularly desirable for use in foodstuff flavors, chewing gum flavors, toothpaste flavors, medicinal product flavors and chewing tobacco flavors. These aroma and taste nuances are particularly useful in curry flavors for foodstuffs and spice flavors for foodstuffs.

Spicy, clove-like, cinnamon-like, floral and minty aromas with warm woody undertones are particularly desirable for perfume aromas and for perfumed article aromas and for aromas of colognes.

U.S. Pat. No. 2,315,046 discloses the use as ingredients in perfumery of certain acylated olefins, which olefins have structures such as:

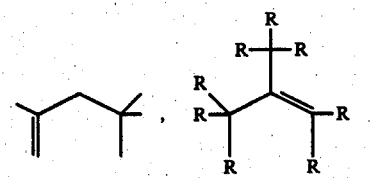

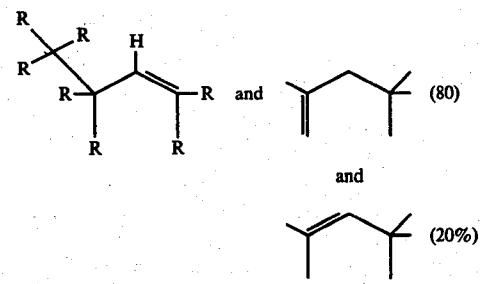

These materials are prepared interalia from commerical diisobutylene according to the reaction:

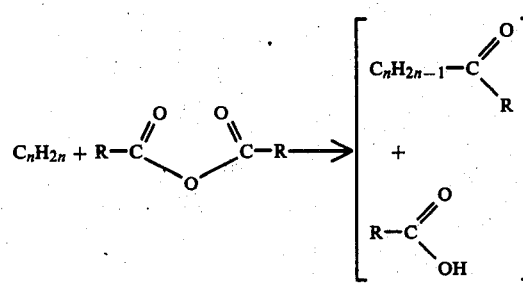

wherein n is 3 or more, and R represents a hydrocarbon radical. Branched unsaturated alpha-beta ketones were known prior to that, for example in U.S. Pat. No. 2,246,032, issued on June 17, 1941, disclosing compounds having the generic structure:

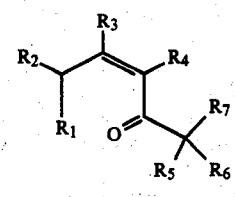

wherein $R_1$–$R_7$ may be any member of a group consisting of hydrogen, aliphatic and cyclo praffinic.

Also, claimed in U.S. Pat. No. 2,315,046 are compounds having the structures:

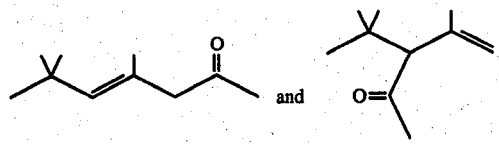

In addition, U.S. Pat. No. 2,463,742 discloses the reaction:

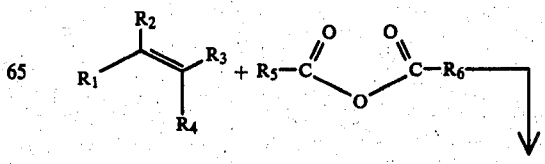

-continued

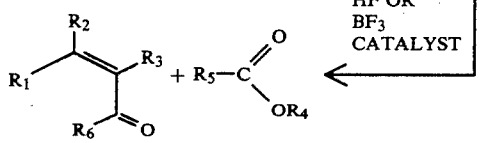

Perfumery compounds are known to have been produced using the Prins reaction. Thus, the paper entitled "The Olefin-Aldehyde Condensation/The Prins Reaction" by Arundale and Mikeska, Chem. Reviews, 51, 505-55 1952, discloses the reaction to form Nopol acetate, thusly:

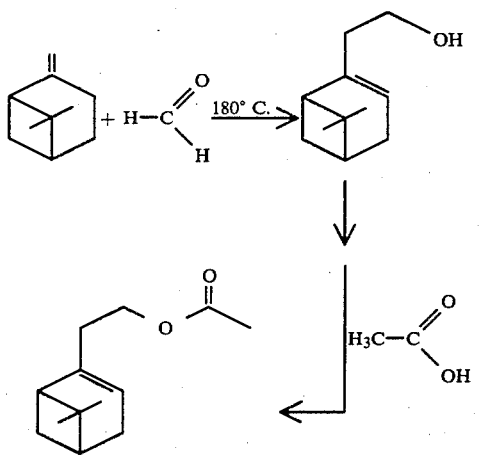

wherein in the reaction, when glacial acetic acid is added to the reaction mass, the Nopol acetate is formed; yet without the use of glacial acetaic acid, Nopol itself is formed.

U.S. Pat. No. 4,100,110 issued on July 11, 1978 (Class 252, Subclass 522) discloses compounds for use in perfumery which are obtained by performing a Prins reaction on longifolene including primary and secondary alcohols, their esters and corresponding aldehydes and ketones. Specifically, in Example 1, column 7 of U.S. Pat. No. 4,100,110 discloses the preparation of compounds having the structures:

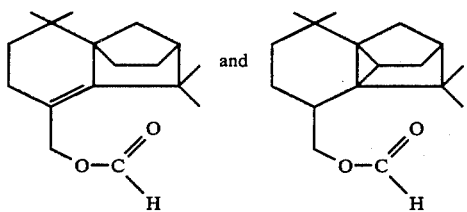

for use in perfumery as a result of their cedarwood-vetiver aroma.

The compounds of the prior art and processes of the prior art are different in kind and yield materials having organoleptic properties different in kind from the compounds of the instant invention.

THE INVENTION

It has now been discovered that novel solid and liquid foodsstuff, chewing gum, medicinal products, toothpaste and chewing tobacco compositions and flavorings therefore having spicy, cumin oil-like, green and herbaceous aroma and taste nuances; as well as novel, solid and liquid perfume, perfumed article and cologne compositions and aromatizing compositions therefore having spicy, clove, cinnamon-like, floral and minty aroma profiles with warm woody undertones; and novel solid and liquid smoking tobacco, substitute smoking tobacco, smoking tobacco article and substituted smoking tobacco article compositions and aroma and flavoring compositions therefore having clove-like and minty aroma and taste nuances both prior to and on smoking in the mainstream and the sidestream may be provided by the utilization of one or more Prins reaction products of diisobutyllene or derivatives thereof defined according to one of the generic structures:

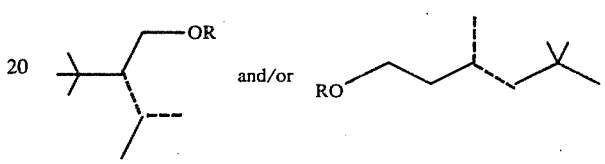

wherein one of the dashed lines represents a carbon-carbon double bond, and the other of the dashed lines represents a carbon-carbon single bond and wherein, "R" represents hydrogen or acetyl. The compounds defined according to the generic structures:

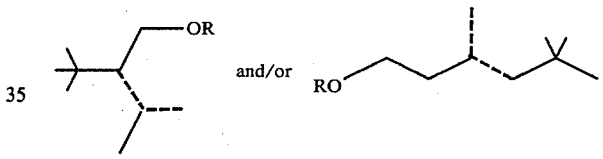

wherein one of the dashed lines represents a carbon-carbon double line, and the other of the dashed lines represents a carbon-carbon single bond and "R" represents hydrogen or acetyl may be prepared by first dimerizing isobutylene according to the teaching of U.S. Pat. No. 2,315,046 or according to the teaching of Japanese Kokai 79,157,510 published on Dec. 12, 1979 (abstracted in Chem Abstracts Vol. 93:25885a) wherein the dimerization of the isobutylene is indicated to take place in the presence of alkylaluminum chloride catalysts such as ethyl aluminum dichloride.

The resulting mixture of dimers of isobutylene may be separated and the individual compounds may be used as is or the resulting mixture may be used in the next reaction wherein the dimer or mixture of dimers is subjected to a Prins reaction with acetic anhydride and either (i) formaldehyde, or (ii) a formaldehyde source such as formalin, paraformaldehyde or trioxane in the presence of (iii) a Lewis acid such as boron trifluoride, boron trifluoride etherate, stannic chloride, ethyl aluminum dichloride or diethyl aluminum chloride according, for example, to the reaction:

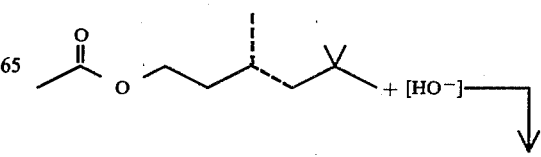

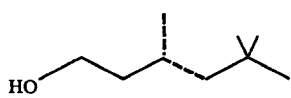

(wherein, one of the dashed lines represents a carbon-carbon double bond and the other of the dashed lines represents a carbon-carbon single bond) and the structure:

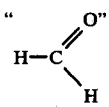

represents formaldehyde itself or a formaldehyde source as such trioxane having the structure:

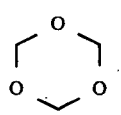

or paraformaldehyde having the structure:

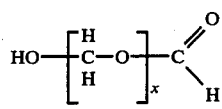

(wherein, "x" represents an integer of from 1 up to 20 or higher).

The resulting product is a mixture defined according to the structures:

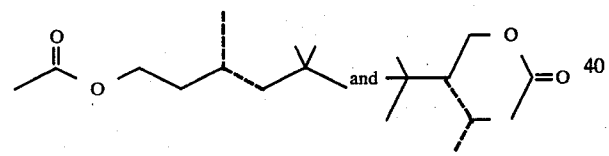

wherein, in the mixture in each of the molecules one of the dashed lines is a carbon-carbon double bond and the other of the dashed lines is a carbon-carbon single bond or individual compounds defined according to the structures:

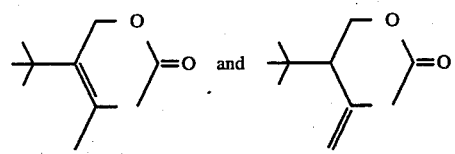

depending upon whether the starting material, the diisobutylene, is a mixture defined according to the structure:

(defining a mixture wherein in the mixture one of the dashed lines is a carbon-carbon double bond and the other of the dashed lines is a carbon-carbon single bond) or a single compound having one of the structures:

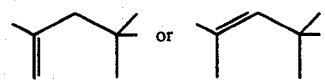

The resulting compounds may be used "as is" for their organoleptic properties; that is, for their spicy and clove aroma nuances in perfumery, or their spicy and clove nuances as flavorants for foodstuffs or their spicy and clove nuances as flavorants, or aromatizers for smoking tobacco and smoking tobacco articles, or the resulting acetates may be hydrolyzed using aqueous base, e.g., sodium hydroxide, potassisum hydroxide, lithium hydroxide, sodium carbonate, potassium carbonate or lithium carbonate whereby alcohols defined according to one of the structures:

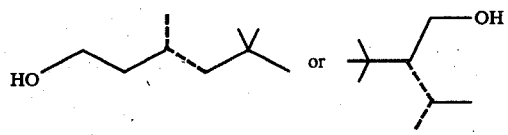

(indicating a mixture wherein in the mixture in one of the molecules one of the dashed lines is a carbon-carbon double bond and the other of the dashed lines is a carbon-carbon single bond) or compounds defined according to one of the structures:

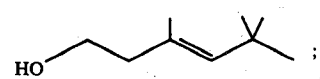

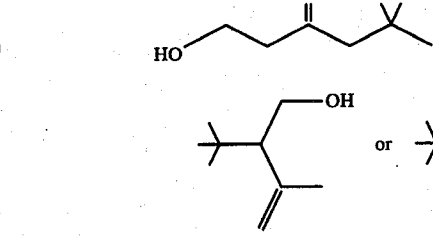

depending on whether the acetate hydrolyzed is defined respectfully according to one of the structures:

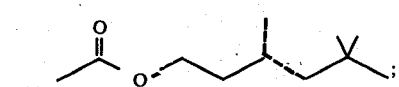

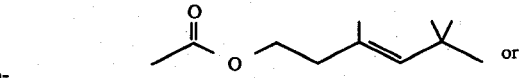

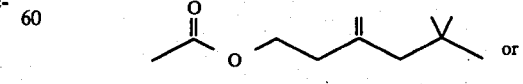

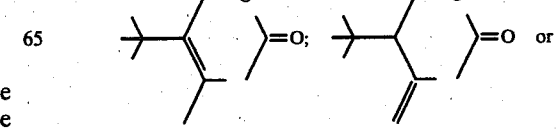

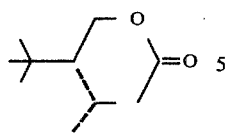

wherein the structures:

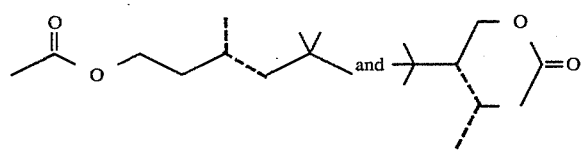

defines a mixture wherein in the mixture in one of the molecules one of the dashed lines represents a carbon-carbon double bond and each of the other of the dashed lines represent carbon-carbon single bonds. This hydrolysis reaction is exemplified according to the following reaction:

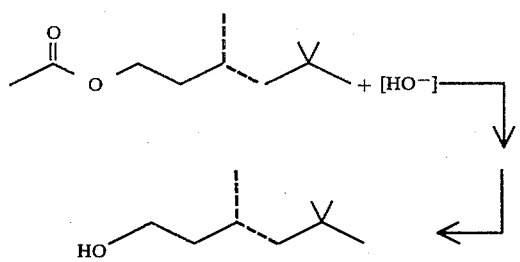

wherein, one of the dashed lines represents a carbon-carbon double bond and the other of the dashed lines represent carbon-carbon single bonds.

The mole ratio of diisobutylene:formaldehyde (as paraformaldehyde or as trioxane) may vary from about 1:2 up to about 2:1 with a preferred mole ratio of about 1:1. The mole ratio of acyl anhydride-diisobutylene may vary from about 1:1 up to about 2:1 acyl anhydride:-diisobutylene with a preferred mole ratio of 1.4-1.5:1 of acyl anhydride:diisobutylene. The concentration of diisobutylene in the reaction mass is preferably from about 1 mole per liter up to about 5 moles per liter.

The concentration of Lewis acid in the reaction mass may vary from about 0.1 moles per liter up to about 0.5 moles per liter.

The reaction temperature may vary from about 50° C. up to about 150° C. depending on the pressure above the reaction mass and depending upon the time desired to complete the reaction for a given particular yield. When higher temperatures are used, the time of reaction required for completion is shorter, however, the yield is lower and the quantity of by-product formed is greater. The most desirable reaction temperature varies between 80° and 110° C. It is most preferable to carry out the reaction at atmospheric pressure. Higher reaction pressures or lower reaction pressures do not give rise to a higher yield or higher conversion rate.

At the end of the reaction, the reaction mass may be "worked-up" in the usual way by means of, for example, distillation or chromatographic separation, e.g., commercial high-pressure liquid chromatography.

In carrying out the hydrolysis reaction the mole ratio of ester to alkali metal hydroxide, e.g., potassium hydroxide, sodium hydroxide or lithium hydroxide, may vary from about 1:2 up to about 2:1 with an excess of alkali metal hydroxide being preferred. That is, it is preferred that the mole ratio of alkali metal hydroxide:ester be about 2:1. It is preferred that the hydrolysis be carried out using highly concentrated base, e.g., from about 30% up to about 50% concentration. The concentration of ester in the reaction mass may vary from about 1 up to about 8 moles per liter with a concentration of 2-3 moles per liter of ester being preferred. The concentration of caustic is preferably double the concentration of ester. Thus, the concentration of caustic may vary from about 3 moles per liter up to about 10 moles per liter with a preferred concentration of caustic being about 5 moles per liter. The temperature of hydrolysis is preferably between about 50° C. up to about 80° C. with a hydrolysis temperature of 65° C. being preferred, at atmospheric pressure. Pressures above atmospheric pressure or below atmospheric pressure may be used for the hydrolysis reaction but using higher or lower pressures does not give rise to any advantage insofar as yield or conversion per unit time is concerned. Indeed, most economically, the reaction pressure for this hydrolysis reaction is preferably 1 atmosphere.

At the end of the hydrolysis reaction, the reaction mass may be appropriately worked up as by pH adjustment and fractional distillation thereby yielding the unsaturated alcohol.

When the Prins reaction products of diisobuytlene and derivatives thereof of my invention are used as food flavors adjuvants, or toothpaste flavor adjuvants, or chewing gum flavor adjuvants, formulating the product composition will also serve to augment or enhance the organoleptic characteristics of the ultimate foodstuff, chewing gum, medicinal product or toothpaste treated therewith.

The term "augment" in its various forms is used herein to mean the supplying, modifying or imparting of a flavor or aroma characteristic, note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

As used herein, the term "foodstuff" includes both solid and liquid ingestible materials which usually do, but need not, have nutritional value. Thus, foodstuffs includes soups, convenience foods, beverages, dairy products, candies, vegetables, cereals, soft drinks, snacks and the like.

As used herein, the term "medicinal products" includes both solids and liquids which are ingestible non-toxic materials which have medicinal value such as cough syrups, cough drops, aspirin and chewable medicinal tablets.

The term "chewing gum" is intended herein to be a foodstuff which is a composition which comprises a substantially water-insoluble, chewable plastic gum base such as chicle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the unsaturated branched ketones of our invention, and, in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is required that any such material be "ingestibly acceptable", and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthically pleasing aroma and taste profile. Such materials, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiarybutyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl cellulose and methyl cellulose; natural and synthetic gums such as gum arabic, gum tragacanth; gelatin, proteinaceous materials, lipids; carbohydrates, starches, pectins, and emulsifiers, e.g., mono-and diglycerides of fatty acids, skim milk powder, hexoses, pentoses, disaccharides, e.g., sucrose corn syrup and the like.

Surface active agents include emulsifying agents, e.g., fatty acids such as, palmitic acid, myristic acid and the like, mono- and diglycerides of fatty acids, lecithin, defoaming and flavor-dispersing agents such as sorbitan monostearate, potassium monostearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like colorants, e.g., carminic acid, cochineal, tumeric, curcumin and the like; firming agents such as aluminum sodium sulfate, calcium chloride and calcium gluconate; texturizes, anticaking agents, e.g., aluminum calcium sulfate and tribasic calcium phosphate; enzymes; yeast foods, e.g., calcium lactate and calcium sulfate; ntrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2pentenoic acid, 2-methyl-cis-3-pentenoic acid; ketones and aldehydes, e.g., octanal, n-decanal, acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexanal, 2-hexenal, isopentanal, hydrocinnamic aldehyde, cis-3-hexenal, 2-heptenal, nonyl aldehyde, citral, 4-(p-hydroxyphenyl)-2-butanone, alpha-ionone, 2-methyl-3-butanone, benzaldehyde, damascone, damascenone, acetophenone, 2-heptanone, o-hydroxyacetophenone, 2-methyl-2-hepten-6-one, 2-octanone, 2-undecanone,, 3-phenyl-4-pentenal, 2-phenyl-2-hexenal, 2-phenyl-2-pentenal, furfural, 5-methyl furfural, cinnamaldehyde, $\beta$-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, fenchyl alcohol, isofenchyl alcohol, phenyl-2-ethanol, $\alpha$-terpineol, cis-trpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl $\alpha$-methylbutyrate, ethyl propionate, ethyl salicylate, trans-2-hexenyl acetate, hexyl acetate, 2-hexenyl butyrate, hexyl butyrate, isoamyl acetate, isopropyl butyrate, dimethyanthranilate, methyl acetate, methyl butyrate, methyl caproate, methyl isobutyrate, $\alpha$-methylphenylglycidate, ethyl succinate, isobutyl cinnamate, cinnamyl formate, methyl cinnamate and terpinenyl acetate; hydrocarbons such as dimethyl naphthalene, dodecane, methyl diphenyl, methyl naphthalene, myrcene, cadinene, limonene, naphthalene, octadecane, tetradecane, tetramethyl naphthalene, tridecane, trimethyl naphthalene, undecane, caryophyllene, 1-phellandrene, p-cymene, 1-$\alpha$-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, $\alpha$-methyl-3-ethylpyrazine, tetramethylpyrazine, trimethylpyrazine; essential oils, such as jasmine absolute, cassia oil, cinnamon bark oil, rose absolute, orris absolute, lemon essential oil, orange essential oil, grapefruit essential oil, Bulgarian rose, oil of dill, oil of caraway, oil of spearmint, yara yara and vanila; lactones such as gammanonalactone; sulfides, e.g., methyl sulfide and other materials such as maltol, and acetals (e.g., 1,1-diethoxyethane, 1,1-dimethoxyethane and dimethoxymethane).

The specific flavoring adjuvants selected for use may be either solid or liquid depending upon the desired physical form of the ultimate product, i.e., foodstuff, whether simulated or natural, and should, in any event, (i) be organoleptically compatible with Prins reaction products of diisobutylene and derivatives thereof of our invention by not covering or spoiling the organoleptic properties (aroma and taste) thereof; (ii) be non-reactive with the Prins reactionn products of diisobutylene and derivatives thereof of our invention; and (iii) be capable of providing an environment in which the Prins reaction products of diisobutylene and derivatives thereof of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, augmented or enhanced. In contradistinction, in the preparation of solid products, e.g., simulated foodstuffs, ingredients capable of providing normally solid compositions should be selected such as various cellulose derivatives.

As well be appreciated by those skilled in the art, the amount of Prins reaction products of diisobutylene and derivatives thereof of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely dificient in natural flavor or aroma. The primary requirement is that the amount selected be effective, i.e., sufficient to augment or enhance the organoleptic characteristics of the parent composition, whether foodstuff per se, chewing gum per se, medicinal product per se, toothpaste per se, or flavoring composition.

The use of insufficient quantities of Prins reaction products of diisobutylene and derivatives thereof of our invention will, of course, substantially vitiate any possibility of obtaining the desired results while excess quantities prove needlessly costly and, in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of Prins reaction products of diisobutylene and derivatives thereof of our invention ranging from a small but effective amout, e.g., 0.02 parts per million (ppm) up to about 50 parts per million (ppm) based on total composition are suitable. Concentrations in excess of the maximum quantity stated are not normally recommended, since they fail to provide commensurate enhancement of organoleptic properties. In those instances, where the Prins reaction products of diisobutylene and derivatives thereof of our invention is added to the foodstuff as an integral component of a flavoring composition, it is, of course, essential that the total quantity of flavoring composition employed be sufficient to yield an effective Prins reaction products of diisobutylene and derivatives thereof of our invention concentration in the foodstuff product.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the unsaturated branched ketones of our invention with, for example, gum arabic, gum tragacanth, carrageenan and the like, and thereafter spray-drying the resultant mixture whereby to obtain the particulate solid product. Pre-prepared flavor mixes in powder form, e.g., a fruit-flavored powder mixes are obtained by mixing the dried solid components, e.g., starch, sugar and the like and the unsaturated branched ketones of our invention in a dry blender until the requisite degree of uniformity is achieved.

It is presently preferred to combine with the Prins reaction products of diisobutylene and derivatives thereof of our invention, the following adjuvants:
Oil of dillweed
Oil of garlic
Oil of capsicum
Oil of cassia
Oil of cloves
Oil of pimenta berries
Oil of mustard
Oil of bay leaves
L-carvone
D-carvone
Spearmint oil
Cumin aldehyde
Cinamaldehyde As olfactory agents, the Prins reaction products of diisobutylene and derivatives thereof, taken alone or in admixture of my invention can be formulated into when the Prins reaction product of diisobutylene and derivatives thereof of our invention are used as food flavor adjuvants, or used as components of a "perfume composition" or can be used as components of a "perfumed article", or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and hydrocarbons other than the Prins reaction products of diisobutylene and derivatives thereof of this invention which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixtures which include odorous substances which lend a particular note to the perfume throughout all stages of evaporation, and substances which retard evaporation; and (d) top notes which are usually low boiling, fresh-smelling materials.

The following examples serve to illustrate our invention, and this invention is to be considered restricted thereto only as indicated in the appended claims.

All parts and percentages given herein are by weight unless otherwise specified.

EXAMPLE I

PREPARATION OF PRINS REACTION PRODUCT OF DIISOBUTYLENE

Reaction:

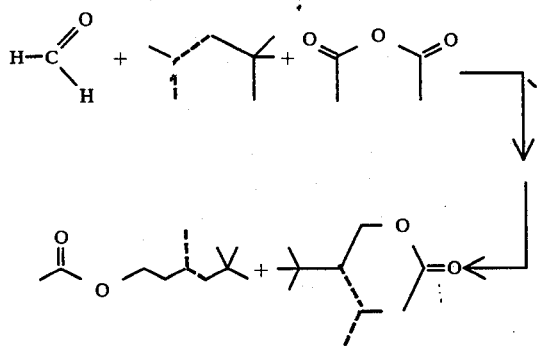

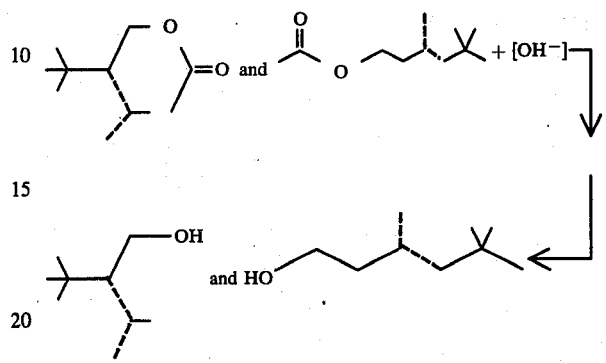

(wherein, in the resulting mixture, in each of the molecules of the mixture one of the dashed lines represents a carbon-carbon double bond, and the other of the dashed lines represents a carbon-carbon single bond).

Into a 5 liter, 3 neck flask equipped with 3 liter addition funnel, stirrer, thermometer and reflux condenser is placed 1428 ml acetic anhydride and 25 ml boron trifluoride etherate. The resulting mixture is heated to 40° C. and while maintaining the temperature at 70° C. over a period of 1 hour, a previously-prepared mixture of 324 grams of paraformaldehyde and 1600 ml diisobutylene is added to the reaction mixture. At the end of the 1 hour period, after addition is complete, the reaction mass is stirred with cooling for a period of 2 hours. At the end of the 2 hour period, with the reaction mass at 27° C., the reaction mass is poured into 1400 ml water. The reaction mass then separates into two phases; an organic phase and an aqueous phase. The organic phase is washed with one (1) liter portion of 10% aqueous sodium hydroxide, followed by water, whereby the pH of the resulting material is 3.5. The reaction mass is then distilled on a 2" stone packed column yielding the following fractions:

| Fraction Number | Vapor Temp. (°C.) | Liquid Temp. (°C.) | Pressure mm/Hg. | Weight of Fraction (g) |
|---|---|---|---|---|
| 1 | 77 | 89 | 4.0 | 249 |
| 2 | 76 | 90 | 3.5 | 396 |
| 3 | 87 | 114 | 3.5 | 347 |
| 4 | 135 | 172 | 3.5 | 288 |

The reaction mass is then subsequently distilled on a fractionation column yielding 15 fractions:

| Fraction Number | Vapor Temp. (°C.) | Liquid Temp. (°C.) | Pressure mm/Hg. | Weight of Fraction (g) |
|---|---|---|---|---|
| 1 | 28 | 90 | — | 86 |
| 2 | 78 | 96 | — | 82 |
| 3 | 43 | 97 | — | 76 |
| 4 | 39 | 94 | — | 66 |
| 5 | 40 | 96 | — | 38 |
| 6 | 44 | 94 | — | 56 |
| 7 | 44 | 93 | 0.9 | 82 |
| 8 | 41 | 98 | 0.6 | 84 |
| 9 | 48 | 104 | 0.9 | 91 |
| 10 | 43 | 108 | 0.7 | 88 |
| 11 | 42 | 115 | 0.6 | 76 |
| 12 | 43 | 128 | 0.7 | 74 |
| 13 | 55 | 160 | 0.7 | 39 |
| 14 | 130 | 163 | — | 16 |
| 15 | 123 | 230 | — | 108 |

Fractions 4–15 are bulked.

EXAMPLE II

PREPARATION OF HYDROLYSIS PRODUCT OF PRINS REACTION PRODUCT OF DIISOBUTYLENE

Reaction:

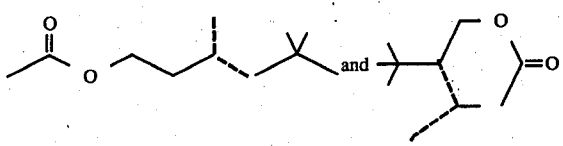

(wherein, in the resulting mixture, in one of the molecules of the mixture 1 of the dashed lines represents a carbon-carbon double bond, and the other of the dashed lines represents a carbon-carbon single bond).

Into a 1 liter reaction flask equipped with stirrer, thermometer and reflux condenser is placed:

(a) 208 grams of the Prins reaction product prepared according to Example I, bulked fractions 4-15 defined according to the generic structures:

(wherein, in the mixture, in each molecule of the mixture, one of the dashed lines represents a carbon-carbon double bond and the other of the dashed lines represents a carbon-carbon single bond).

(b) 190 grams 50% aqueous sodium hydroxide
 1 gram of Aliquat ® 336 (quaternary ammonium salt; cetyl trimethyl ammonium chloride manufactured by the General Mills Chemical Company of Minneapolis, Minnesota)

The reaction mass is heated to a 100° C. for 4 hours, thus yielding two phases; an organic phase and an aqueous phase. The reaction mass is cooled to room temperature and placed in a separatory funnel. The organic phase is separated from the aqueous phase, and the aqueous phase is washed with 475 ml anhydrous diethyl ether. The ether is evaporated from the ether extract and combined with the organic phase. The resulting organic phases are washed with 375 ml portions of water. The organic phase is then washed as follows:

(a) One 500 ml portion of water;
(b) 475 ml portions diethyl ether;
(c) 375 ml portions water;
(d) 175 ml portions saturated salt.

The resulting organic phase is then dried over anhydrous magnesium sulfate, evaporated and distilled. One fraction results from the distillation boiling at 47° C. and 1.6 mm Hg. pressure. The yield is 91 grams.

EXAMPLE III

DILL SPICE FLAVOR

The following formulation is produced:

| Ingredients | Parts by Weight |
| --- | --- |
| Oil of dillweed | 84.5 |
| Oil of garlic | 1.75 |
| Oil of capsicum | 3.75 |
| Oil of cassia | 2.50 |
| Oil of cloves | 2.50 |
| Oil of pimenta berries | 2.50 |
| Oil of mustard | 1.25 |
| Oil of bay leaves | 1.25 |
| L-carvone | 4.60 |
| D-carvone | 3.80 |
| Cumin aldehyde | 2.51 |

The formulation is split into three parts. To one part is added the Prins reaction product mixture produced according to Example I, to the second part is added a derivative of the Prins reaction product mixture prepared according to Example II. To the third part, nothing is added. The three formulations are prepared at levels of 5 ppm, 10 ppm and 20 ppm in water and in tomato ketchup. The formulations containing the Prins reaction product of Example I and the Prins reaction product derivatives of Example II cause the flavor to be much more full bodied and more natural-like, as the flavor has cumin oil-like, and minty nuances in addition to the "natural" dill-like nuances. The "natural" aspects of these flavors, together with the caraway-like, cumin oil-like, and minty nuances are missing in the flavor that does not contain the Prins reaction product or the Prins reaction product derivatives produced according to either of Examples I or II.

EXAMPLE IV

SPEARMINT FLAVOR

The following spearmint flavor is produced.

| Ingredients | Parts by Weight |
| --- | --- |
| Spearmint oil | 42.0 |
| L-carvone | 12.0 |
| D-carvone | 8.0 |

This formulation is split into three portions. To the first portion and to the second portion, 4.0 parts by weight, respectively, of the Prins reaction products and Prins reaction product derivatives prepared according to Examples I and II, respectively, are added. To the third portion, nothing is added. The flavors are tested at levels of 5 ppm, 10 ppm and 20 ppm in water and in chewing gum which heretofore was unflavored. The chewing gum containing the flavor formulations with the Prins reaction product derivatives and Prins reaction products produced according to Examples I and II have more natural-like, minty aromas and tastes, with excellent and caraway and dill-like nuances present. The formulations have great amounts of "natural mintiness" which are not only "natural-like" but which are also "long lasting" and which remain of high strength throughout the chewing procedure of the chewing gums.

EXAMPLE V

A toothpaste is prepared according to the following formula:

| Ingredients | Parts by Weight |
| --- | --- |
| Sorbitol (70% soln.) | 20.00 |
| Sodium saccharin | 0.21 |
| Veegum (colloidal magnesium aluminum silicate) | 0.40 |
| Precipitated urea/formaldehyde condensate (abrasive) | 30.00 |
| Prins reactions product or Prins reaction product derivatives prepared according to Example I or II, respectively | 1.00 |
| Sodium carboxymethycellulose | 1.30 |
| Glycerine | 10.00 |
| 1.2-bis($N^5$—p-chlorophenyl-$N^1$—biguanido) ethane digluconate | 0.70 |
| Polyoxyethylene sorbitan (20) monoisostearate | 1.50 |
| Distilled water | balance to 100 |

This toothpaste when used in the normal manner, is not only effective in retarding the formation of dental plaque and produce appreciably lower levels of stain on the teeth than does chlorhexidine; but, in addition, has an excellent sweet, spicy, minty, herbaceous, bread-like, caraway-like, cumin-like and dill-like taste profiles.

EXAMPLE VI

A mouthwash in accordance with the present invention is formulated as follows:

| Ingredients | Parts by Weight |
| --- | --- |
| Ethyl alcohol (95% in water | 12.00 |
| Cetyl pyridinium chloride | 0.10 |
| Polyoxyethylene (20) sorbitan monooleate | 0.12 |
| Sodium hydroxide (10% in water) | 0.02 |
| Sodium saccharin | 0.055 |
| Prins reaction product or Prins reaction product derivative prepared according to Example I or II, respectively | 0.16 |
| 1,2-bis($N^5$—p-chlorophenyl-$N^1$—biguanido) ethane dihydrochloride | 0.20 |
| Color | 0.50 |
| Sorbitol (70% in water) | 12.00 |
| Distilled water | balance to 100 |

When used in the normal manner to rinse the mouth, these products are effective not only in retarding the formation of dental plaque and produce an appreciably lower level of stain on the teeth than does chlorhexidine; but also have excellent sweet, spicy, minty, cumin-like, herbaceous, bread-like, caraway-like and dill-like taste profiles.

EXAMPLE VII

Chewing gum in accordance with the present invention are formulated as follows:

| Ingredients | Parts by Weight |
| --- | --- |
| Gum base | 21.30 |
| Ester Gum | 6.40 |
| Coumarone resin | 9.60 |
| Dry latex rubber | 3.20 |
| Paraffin wax (M.P. 180° F.) | 2.10 |
| Sugar | 58.45 |

| Ingredients | Parts by Weight |
|---|---|
| Corn syrup (Baume 45) | 18.20 |
| Prins reaction product or Prins reaction product derivatives prepared according to Example I or II, respectively | 1.5 |
| 1,2-bis($N^5$—p-chlorophenyl-$N^1$— biguanido) ethane diacetate | 1.00 |

Chewing these gums in the normal manner not only retards the formation of dental plaque and produce appreciably less staining on the teeth than does chlorhexidine but also gives rise to a pleasant, long-lasting and intense sweet, cumin-like, spicy, minty, herbaceous, bread-like caraway-like and dill-like taste profile.

What is claimed is:

1. A process for augmenting or enhancing the aroma or taste of a foodstuff comprising the step of adding to said foodstuff from 0.02 parts per million up to about 50 parts per million based on the total composition of a mixture of compounds containing compounds defined according to the structures:

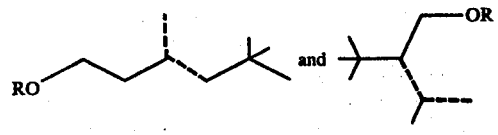

wherein in the mixture, in each of the compounds, one of the dashed lines is a carbon-carbon double bond and the other of the dashed lines is a carbon-carbon single bond and in both compounds, the moiety "R" is the same and "R" represents a moiety selected from the group consisting of hydrogen and acetyl.

2. The process of claim 1 wherein in the mixture of compounds, "R" represents hydrogen.

3. The process of claim 1 wherein in the mixture of compounds, the moiety "R" represents acetyl.

* * * * *